US005350369A

United States Patent [19]

Workman et al.

[11] Patent Number: 5,350,369

[45] Date of Patent: Sep. 27, 1994

[54] APPARATUS AND METHODS FOR CLOSED COLLECTION OF HUMAN WASTES

[75] Inventors: James P. Workman, Spring Hill, Kans.; Thomas S. Hargest, Charleston, S.C.

[73] Assignee: Burke, Inc., Mission, Kans.

[21] Appl. No.: 778,516

[22] Filed: Oct. 18, 1991

Related U.S. Application Data

[62] Division of Ser. No. 314,716, Feb. 23, 1989, Pat. No. 5,058,222.

[51] Int. Cl.[5] ........ A61M 1/00

[52] U.S. Cl. ........ 604/327; 604/317; 4/316; 4/484; 5/604

[58] Field of Search ........ 4/316, 484, 452; 5/604, 5/605, 606, 607, 610, 611, 612, 616, 617, 463, 464; 128/760, 761; 604/317-328

[56] References Cited

U.S. PATENT DOCUMENTS

| | | | |
|---|---|---|---|
| 801,117 | 10/1905 | Stow | 5/604 |
| 1,589,889 | 6/1926 | Mas et al. | 5/604 |
| 1,682,266 | 8/1928 | Daggy | 604/331 |
| 2,749,558 | 6/1956 | Lent et al. | 4/316 |
| 2,932,831 | 4/1960 | Keathley, Sr. et al. . | |
| 3,285,145 | 4/1975 | Ericson . | |
| 3,422,985 | 1/1969 | Rinehart | 4/316 |
| 3,475,767 | 11/1969 | Friesen et al. . | |
| 3,577,989 | 5/1971 | Anderson . | |
| 3,619,822 | 11/1971 | Carmichael . | |
| 3,719,962 | 5/1973 | Burkley . | |
| 3,729,107 | 4/1973 | Present . | |
| 3,777,729 | 12/1973 | Raitto . | |
| 3,781,922 | 1/1974 | Ericson . | |
| 3,802,418 | 4/1974 | Clayton . | |
| 3,878,572 | 4/1975 | Eriksson . | |
| 3,920,179 | 11/1975 | Hall . | |
| 3,933,636 | 1/1976 | Daniels . | |
| 4,067,335 | 1/1978 | Silvanov . | |
| 4,091,930 | 5/1978 | Buchner et al. . | |
| 4,139,488 | 2/1979 | Knotik et al. . | |
| 4,244,920 | 1/1981 | Manschot et al. . | |
| 4,271,546 | 6/1981 | Martin . | |
| 4,394,784 | 7/1983 | Swenson et al. . | |
| 4,449,984 | 5/1984 | Cruz . | |
| 4,495,209 | 1/1985 | Whiteside . | |
| 4,539,793 | 9/1985 | Malek . | |
| 4,631,762 | 12/1986 | Eugett . | |
| 4,660,354 | 4/1987 | Lancaster et al. . | |
| 4,684,913 | 8/1987 | Austin . | |
| 4,754,508 | 7/1988 | Nishiguchi . | |
| 4,821,348 | 4/1989 | Pauna . | |
| 4,920,587 | 5/1990 | Kerr | 5/604 |
| 4,955,090 | 9/1990 | Stefan | 4/316 |
| 4,977,629 | 12/1990 | Jones | 5/463 |
| 5,033,130 | 7/1991 | Dehaese | 4/452 |

*Primary Examiner*—Randall L. Green
*Assistant Examiner*—Rob Clarke
*Attorney, Agent, or Firm*—Kokjer, Kircher, Bowman & Johnson

[57] ABSTRACT

A collection, storage and disposal system for human wastes. An externally positionable patient interface directs wastes through a conduit to a storage container. Accumulated wastes are sealed within the storage container to prevent cross-contamination. The patient interface is extendable through an aperture formed within a seat portion of a support structure which can be converted between bed and chair configurations. A mattress has a foam insert which may be selectively inflated to maintain desired supporting pressure for the patient and to provide a resilient support surface should deflation of the mattress occur.

1 Claim, 6 Drawing Sheets

20
22
28
30
32
34
44
46
50
56
60
62
64
66
70
113
114
136
42a
42b
26
54
58

20
22
24
26
28
30
32
34
36
38
40
42a
42b
46
48
50
52
56
58
60
62
64
66
68
72
74
76
78
80
106
108
113
114
3.

APPARATUS AND METHODS FOR CLOSED COLLECTION OF HUMAN WASTES

This is a divisional application of application Ser. No. 07/314,716, filed on Feb. 23, 1989, and entitled "Support Structure Containing Closed System for Collection of Human Wastes", now U.S. Pat. No. 5,058,222.

BACKGROUND OF THE INVENTION

This invention relates in general to human waste disposal systems and, more particularly, to an apparatus and method for the collection, containment and disposal of human wastes.

Two basic devices currently exist for collecting and disposing of defecated wastes from patients who, because of physical infirmity or other reasons, are unable to utilize a conventional toilet. A bed pan configured to the patient's buttocks is one device which is commonly used. Utilization of such a device, however, is necessarily limited to those patients who are able to anticipate the need for its use. Senile, unconscious or seriously ill individuals, as well as those who are unable to call for assistance would be unable to use a bedpan. Incontinent patients, that is, those patients with uncontrolled bladder and bowel movements, do not have sufficient advance warning to call for or safely position a bed pan without risk of an accident occurring.

Those who are able to use a bed pan must endure the embarrassment of summoning a nurse to bring the device and position and remove it from beneath the patient. Moreover, the use of a bed pan while the patient is in bed requires that the individual assume either a horizontal position or a sitting position with the legs extending horizontally. Either position is an unnatural physiological position and many patients find it difficult to adapt to the use of a bed pan.

In addition to the problems that the bed pan presents for the patient, assisting personnel likewise are subjected to an objectionable situation. First, the nurse may be required to physically lift the individual to ensure proper placement. After use, the individual must be cleaned and the pan removed from beneath the patient without spilling its contents. This can be a difficult proposition at best as the nurse must lean over the bed and somehow support the patient while gently removing the device.

Bed pans also expose assisting personnel to possible contamination from the pan contents. When the patient is afflicted with a communicable disease such as hepatitis or acquired immune deficiency syndrome (AIDS), such cross contamination may be a life threatening exposure. Although protective items such as caps, gowns, rubber gloves and masks may be utilized, the risk of contamination remains great because the laborious process required to position and remove the pan may cause a breach of contamination safeguards. Moreover, this recurring risk is encountered by nursing staff each time a patient has a bowel movement, which can be as often as twenty to thirty times per day.

Adult diapers have been used as an alternative to bed pans, especially with seriously ill patients. Again, placement and removal of a device such as this can be physically taxing for both the nurse and the patient. Conscious patients must endure the discomfort and embarrassment of a soiled diaper and assisting personnel are exposed to the dangers of cross-contamination when changing the diaper and cleaning up. Because of the many problems which result from usage of diapers, they are particularly undesirable solution for the patient who is unable to utilize toilet facilities.

One alternative to the bed pan and adult diaper is described in U.S. Pat. No. 4,067,335 which discloses a device which is fixed internally of an individual and coupled with an elongated receiving and storage tube. As a portion of the tube is filled, it is sealed and may be separated from the unfilled portion for disposal. The invasive nature of this device, however, may cause abrasion and pressure sores as well as patient discomfort. Skilled assistance may also be required to ensure proper internal placement.

SUMMARY OF THE INVENTION

It is an object of this invention to provide a human waste collection device which may be utilized by a patient while in a bed or chair and which may be operated by the patient without requiring the assistance of nursing or other personnel.

It is another object of this invention to provide a human waste collection device which may be utilized by a patient while in a bed or chair and which may be operated by the patient without requiring the assistance of nursing or other personnel.

It is another object of this invention to provide a human waste collection device which provides for the collection, containment and disposal of the wastes in a manner which substantially reduces the exposure of assisting personnel to the risk of cross-contamination.

It is also an object of this invention to provide a waste collection device which stores an accumulation of generated wastes remotely from the patient so that disposal of the wastes takes place at less frequent intervals to reduce the risk of cross-contamination.

It is a further object of this invention to provide a support structure which incorporates a waste collection and storage device and which may be used as either a bed or chair so that an individual may comfortably remain on the structure for an extended period of time and may attend to bodily functions without leaving the support structure.

It is yet another object of this invention to provide a noninvasive waste collection and storage device which may be used by incontinent individuals without requiring continual assistance by nursing personnel.

It is a yet further object of this invention to provide an externally positionable waste collection device which may be utilized with a support structure such as a bed or chair and which seals the collected wastes to prevent cross-contamination during disposal of the collected wastes.

It is a still further object of this invention to provide an air mattress which is selectively inflatable to provide the optimum resiliency for reducing the incidence of pressure sores on patients and which provides a resilient support surface to maintain patient comfort should deflation of the mattress occur.

To accomplish these and other related objects of the invention, a support structure is provided which may be converted between bed and chair configurations. The support structure is provided with a waste collection, containment and disposal mechanism for the closed collection of human wastes to substantially reduce the likelihood of cross-contamination. The mechanism comprises a conduit, means such as an interfacing saddle coupled with one end of the conduit and externally engageable with an area at least partially surrounding a human anal region for directing excreted wastes to the conduit, and a disposable container coupled with the other end of the conduit for collecting the excreted wastes conveyed through the conduit. The container is sealable for disposal without danger of spillage of the contents. The support structure also includes an aperture in a support surface of the structure which may be moved from a normally closed position to an open position to allow the interfacing saddle to be brought into engagement with the patient's anal region.

Another feature of the invention is an inflatable mattress for the support structure which includes a foam-like insert for providing a resilient supporting surface should mattress deflation occur. The mattress includes separately adjustable regions which may be selectively inflated to maintain the optimum resiliency for reducing pressure sores. Chambers along the side edges of the mattress may be inflated to prevent the patient from rolling off the support structure.

BRIEF DESCRIPTION OF THE DRAWINGS

In the accompanying drawings in which like reference numerals are used to indicate like parts in the various views.

DESCRIPTION OF THE PREFERRED EMBODIMENT

Figure 2:
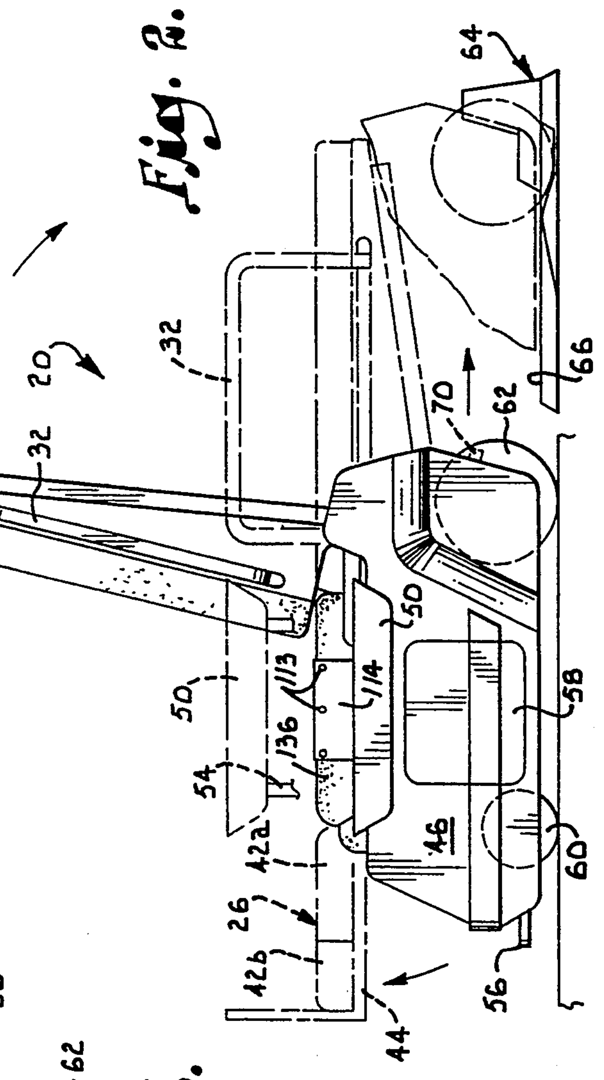
FIG. 2 is a side elevation view of the support structure shown in FIG. 1, with fragmentary lines illustrating conversion of the support structure from a chair to a bed configuration.
Figure 1:
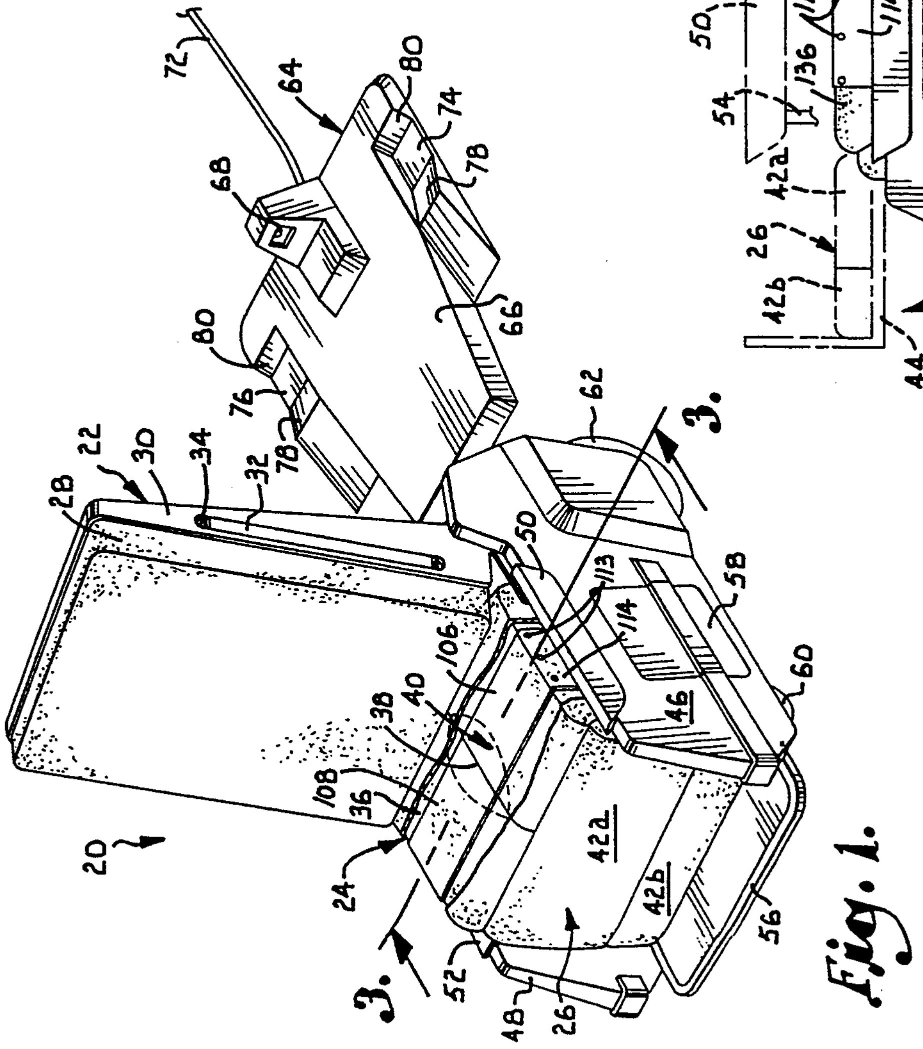
FIG. 1 is a side perspective view of a patient support structure which incorporates a closed waste collection system of the present invention, the support structure being adjusted to a chair configuration.

Turning now to the drawings in greater detail and initially to FIGS. 1-2, an adjustable patient support structure incorporating a waste collection, containment and disposal system of the present invention is represented generally by the numeral 20. Support structure 20 includes a head portion 22, a seat portion 24 and a foot portion 26 which cooperatively define a support surface for the patient. The head and foot portions 22 and 26 are adjustable so that the support structure may be moved between a bed and a chair configuration, as illustrated in FIG. 2. Seat portion 24 may also be adjustable to facilitate positioning of the patient in the desired orientation.

Head portion 22 includes a cushion or mattress 28 coupled with an adjustable support frame 30. The support frame includes a pair of extendable rails 32 housed within openings 34 formed on opposed sides of the frame. Rails 32 are normally maintained in a recessed position when the support structure 20 is positioned in a chair configuration. When the structure is positioned in a bed configuration the rails may be extended outward and then pivoted upward to lock in a position to serve as side rails.

Figure 4:
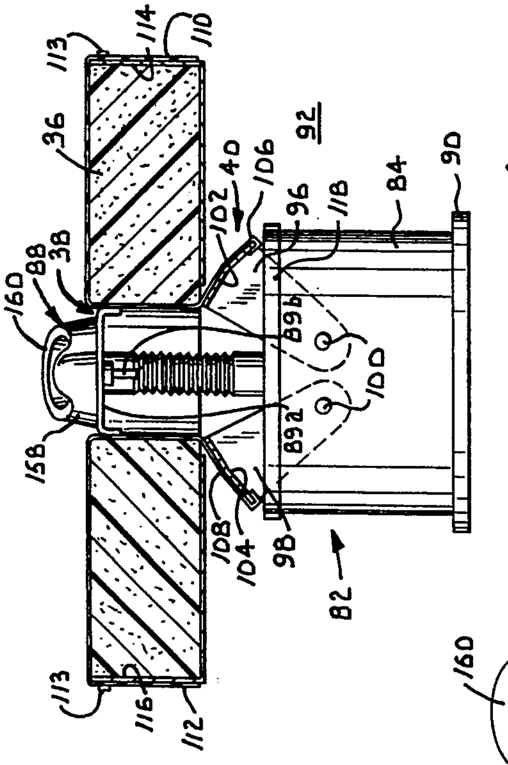
FIG. 4 is a vertical cross-sectional view similar to that shown in FIG. 3 but with a portion of the waste collection system shown elevated through an aperture in the support structure.
Figure 3:
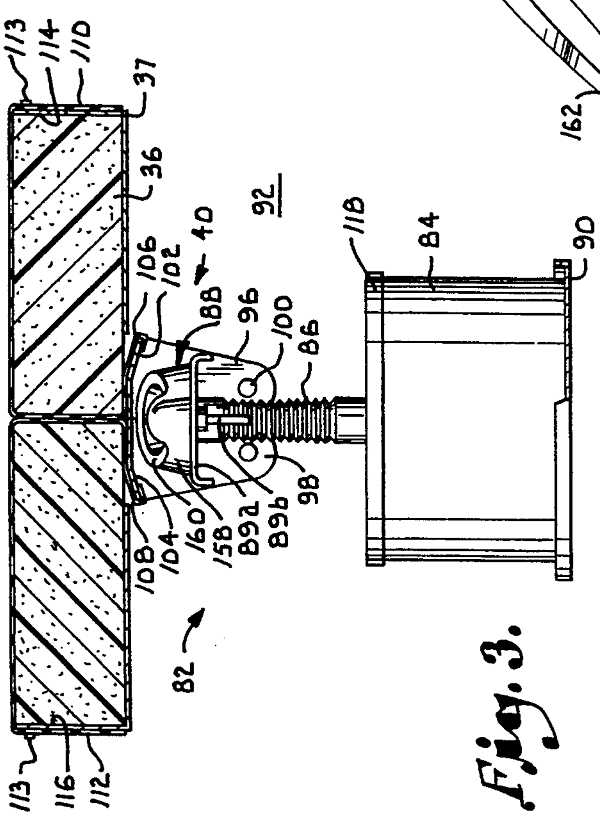
FIG. 3 is a vertical cross-sectional view of the support structure taken along line 3—3 in FIG. 1 and with portions of the support structure and collection system removed to illustrate arrangement of various components.

Seat portion 24 includes a cushion or mattress 36 on a support frame 37 (FIGS. 3 and 4). The mattress includes a centrally positioned vertically extending aperture 38 and an opening mechanism 40 for moving the aperture between open and closed positions. Foot portion 26 also includes a cushion or mattress which is divided into two segments 42*a* and 42*b* and is coupled with an adjustable support frame 44. Mattresses 28, 36 and 42 may be interconnected or separated as desired. Support frames 30 and 44 are adjustable between generally horizontal positions and generally vertical positions.

Side frame members 46 and 48 which enclose portions of the sides of support structure 20 include a pair of armrests 50 and 52 which are positioned adjacent the seat portion 24. Armrests 50 and 52 each include a pair of telescoping support posts 54 which allow vertical extension of the armrests. The armrests may also be moved inwardly and outwardly to other desired positions. A footrest 56 extends horizontally between the side frame members 46 and 48 below the foot portion 26 for use when support structure 20 is in the chair configuration. An access panel 58 is provided in side frame member 46 to permit access to an interior compartment which houses selected components of the waste collection, containment and disposal system.

Mobility of support structure 20 is provided by a pair of front wheels 60 and a pair of larger diameter rear wheels 62. Powered propulsion of either the front or rear wheels may be provided by a suitable drive mechanism (not shown) such as a singular motor or individual motors at each rear wheel. Steering may be accomplished by a joy stick or other four axis control device which allows for forward, rearward and sideward directional control by individually powering or braking each of the drive wheels. Suitable electronic, pneumatic, hydraulic or mechanical components may be used to accomplish the driving or braking of each drive wheel. The control device could be a pendant device or a device integral with one of the armrests 50 or 52. A self-contained power source 63 (FIG. 13) such as NiCad or gel cell batteries is preferably utilized for powering the drive mechanism as well as the various components of support structure 20 which require a power source.

A floor mounted recharging unit 64 is provided for recharging the self-contained power source. Unit 64 comprises a generally planar base 66 and a female receptacle 68 supported above the base for mating with a male receptacle 70 provided on support structure 20. Recharger 64 includes standard internal recharging components which are coupled by a power cord 72 to a suitable source of electrical energy. Suitable recharging components include those found in a Schauer brand recharger bearing model number SR5024WC. Male receptacle 70 is coupled with the self-contained power source on support structure 20. Base 66 includes a pair of spaced apart ramps 74 and 76 which receive rear wheels 62 to position male receptacle 70 within female receptacle 68 when recharging of the self-contained power source is desired. The ramps 74 and 76 include inclined surfaces 78 and 80 which block the rear wheels to prevent inadvertent disengagement of the receptacles during recharging.

Figure 13:
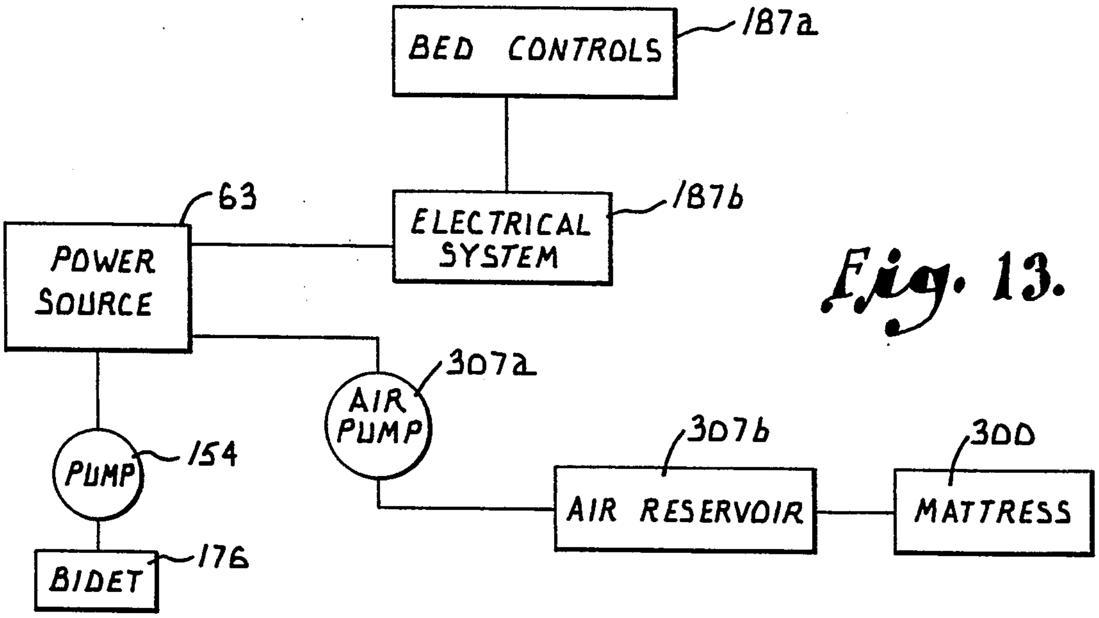
FIG. 13 is a diagrammatic view showing a schematic representation of the operating systems of the present invention.

Turning additionally to FIGS. 3-4 and 13, one embodiment of a waste collection apparatus which is used in conjunction with support structure 20 will now be described. The waste collection apparatus is broadly designated by the numeral 82 and includes a storage container 84 which is connected by a conduit 86 to a patient interfacing saddle 88. The conduit 86 may be rigid to support the saddle or a suitable frame may be provided for the same purpose. Preferably, an extendable platform 89*a* is provided to engage the undersurface and support saddle 88. Platform 89*a* is connected to a linear actuator 89*b* or other suitable device for raising and lowering the platform 89*a* to elevate the interfacing saddle 88 through the aperture 38 provided in the overlying seat mattress 36. Apparatus 82 is positioned on a platform 90 within an internal compartment 92 of the support structure. Opening mechanism 40 moves aperture 38 between its normally closed position shown in FIG. 3 and an open position shown in FIG. 4 to permit elevation of saddle 88 into contacting engagement with the patient's buttocks. Mechanism 40 comprises adjacently positioned pivoting supports 96 and 98 which are connected to a suitable frame (not shown) by pivot pins 100. The pivoting supports have upper surfaces 102 and 104 which are sized and shaped for placement in an opening 105 provided in mattress frame 37 to support the overlying mattress 36. A suitable mechanism (not shown) is coupled with the supports 96 and 98 for effecting pivoting movement thereof between the closed position shown in FIG. 3 and the open position shown in FIG.

The Opening mechanism 40 also includes flexible bands 106 and 108 which have first ends 110 and 112 attached by suitable connectors 113 to the opposed vertical walls 114 and 116 of the mattress support frame 37. The bands extend inwardly along the mattress 36 upper surface to the centrally positioned aperture 38 and downward along the opposed sidewalls of the aperture. The second ends of the bands are then attached to the upper surfaces 102 and 104 of the respective pivoting supports. Pivoting of supports 96 and 98 to the open position thus causes the bands to exert a spreading force on the sidewalls of the aperture to form an opening for passage of saddle 88. Likewise, pivoting of supports to the closed position allows return of the aperture to a closed position.

Figure 6:
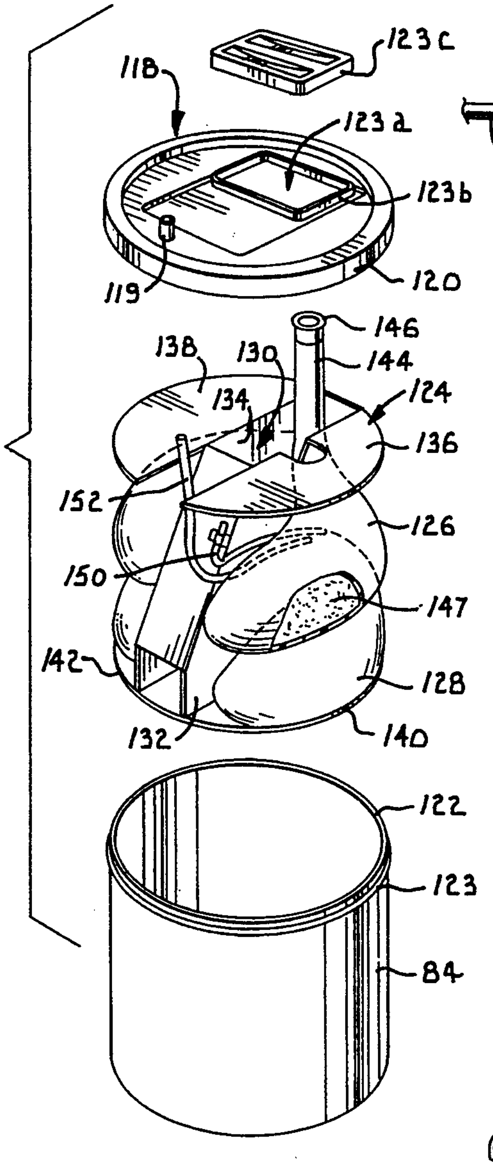
FIG. 6 is an exploded perspective view of a storage container of the waste collection system.

Turning additionally to FIG. 6, the container 84 for storing and sealing the wastes is cylindrical in configuration and formed from plastic or other suitable material. Other configurations may also be used for the container. A removable discoidal lid 118 is provided to enclose the open top of container 84. Lid 118 includes a fitting 119 and a downturned peripheral skirt 120 for engaging an out-turned lip 122 and locking ring 123 which are provided on container 84. Also included on the lid is a rectangular opening 123*a* defined by a raised wall 123*b*. A sealing lid 123*c* is provided for sealingly closing the opening 123*a*.

The internal components of the storage container 84 comprise a supporting liner 124 of paperboard or like construction, a disposable waste collecting bag 126 which straddles liner 124, and a bidet reservoir bag 128 which supports bag 126 and also straddles the liner. Liner 124 includes a central disposal well 130 which is defined by spaced apart vertical walls 132 and 134 and is open at the top. A pair of foldable arcuate ear flaps 136 and 138 are attached to the upper edges of the walls. Similarly, a pair of arcuate ear flaps 140 and 142 project from the lower edges of the vertical walls. Each pair of flaps is sized and shaped to fit tightly within storage container 84. The liner 124 is preferably constructed so that it may be folded flat for shipping.

The disposable waste collecting bag 126 is formed from a flexible, impermeable material. Bag 126 is constructed in a configuration to straddle the central disposal well 130 and includes an elongated throat 144 which extends upwardly and terminates in a fitting 146. A gelling material 147 may be included within the bag to solidify the accumulated waste material. Gelling material 147 may comprise various known hygroscopic materials and may be in a powder, granule, pellet or other suitable form. The gelling material may be vertically spaced along the inner surface of the bag if desired or may be periodically added to the bag during usage. The gelling material may also include a deodorizer such as an olfactory suppressant to mask the odor of the wastes which are directed to the bag.

Figure 9:
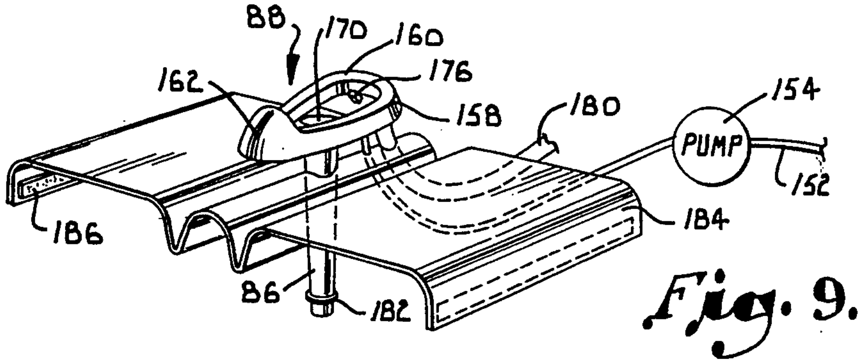
FIG. 9 is a front perspective view of the waste collection system shown in FIGS. 3-5.

Bidet reservoir bag 128 is also configured to straddle the central disposal well 130 and may be constructed from material similar to that used for waste collecting bag 126. Bidet bag 128 includes a vent tube 150, and a tube 152 which is coupled with a fluid pump 154 (FIG. 9). Instead of positioning the bidet bag 128 in the storage container, it may be desired to place a fluid reservoir elsewhere on support structure 20. This would permit the container to be dedicated if desired to the collection f wastes within bag 126.

Figure 5:
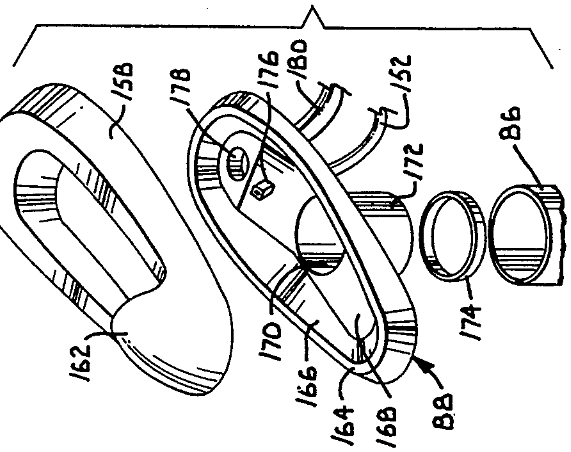
FIG. 5 is an exploded perspective view of an interfacing saddle of the waste collection system.

The construction of interfacing saddle 88 which is coupled with waste collecting bag 126 by conduit 86 can best be seen by reference to FIG. 5. The saddle includes a patient interface 158 which has an elongated ring shape with an open central region. A top surface 160 of interface 158 is generally flat and is configured to sealingly engage the buttocks or anal region of the patient. A forward end of the interface may optionally include an upwardly projecting splash guard 162.

The saddle 88 also includes a generally rigid basin 164 on which the interface 158 is mounted. Basin 164 includes a centrally sloping inner wall 166 and a bottom 168 which slopes toward a drain opening 170. Opening 170 is coupled with a drain tube 172 which extends from the basin and is coupled with conduit 86 by a suitable band clamp 174. A bidet spray nozzle 176 is coupled to pump 154 by the flexible tubing 152 and is mounted on the bottom 168 for directing a stream of cleansing fluid from the bidet reservoir bag 128 to the patient's anal region. Drain opening 170 is positioned for the passage of excreted waste as well as the expended cleansing fluid. An opening 178 is also provided in the bottom 168 of basin 164 for directing a stream of air or other drying medium from conduit 180 into the basin 164.

Turning additionally to FIG. 9, the lower end of conduit 86 is sized for coupling with the elongated throat 144 of bag 126 and includes a connecting ring 182. The conduit is constructed from flexible and compressible material for compact storage. The inner surface of conduit 86 includes a material having a low coefficient of friction which prevents adherence of wastes passing through the conduit. The low coefficient of friction material may be a coating of silicon or other suitable material. Alternately, a layer of suitable material may be coextruded as the inner layer of the conduit during manufacture. A similar material may be applied to the inner surface of waste collecting bag 126.

A disposable apron 184 is also provided to shield the mattress 36 from contamination during utilization of the waste collection apparatus 82. Apron 184 may be formed from suitable liquid impermeable material and includes openings for conduit 86, tubing 152 and conduit 180. Connector strips 186 are also provided to releasably secure the apron to the mattress.

It can be seen that support structure 20 provides a support surface which may be adjusted between bed and chair positions to place a patient in sitting, prone and various intermediary positions. Structure 20 also advantageously provides for the collection, containment and disposal of wastes generated by the patient so that the patient need not leave the structure to attend to bodily functions. The waste collection apparatus 82 may be operated without the assistance of nursing personnel and collects and stores the wastes in a manner which substantially reduces the risk of cross-contamination.

In use, the waste collection apparatus 82 is maintained in its lowered position until needed by the patient. When the patient needs to attend to bodily functions, the patient operates suitable controls 187*a* (FIG. 13) coupled with the operating electrical system 187*b* (FIG. 13) to position the support structure 20 in a chair-like or other desired configuration. The operating controls are then utilized to open the aperture and elevate the collection apparatus. Opening of the aperture is accomplished by outward pivoting of supports 96 and 98 and resulting compression of the aperture sidewalls by bands 106 and 108. The platform 89*a* is then elevated by actuator 89*b* to raise interfacing saddle 88 through the opening formed in the aperture. The top surface 160 of saddle interface 158 is preferably brought into engagement with the patient's buttocks to at least partially surround the anal region. Wastes are then collected in basin 164 and directed through opening 170 into conduit 86 where they are conveyed to the waste collecting bag 126 in storage container 84. The wastes are thus completely segregated by the collection apparatus 82 to substantially reduce the likelihood of cross-contamination. Any wastes which escape from saddle 88 are maintained on apron 184 which may be disposed of to maintain a contamination free environment on the support structure 20.

When defecation has been completed, the patient's anal region is cleansed by directing a stream of cleansing fluid from bidet reservoir bag 128 through nozzle 176 positioned in the saddle 88. The expended fluid is then directed through opening 170 and conveyed to waste collecting bag 126 by conduit 86. A stream of a drying medium such as air is then directed through opening 178 in saddle 88 to dry the anal region.

After cleansing and drying have been completed, the saddle is lowered through the aperture and the pivoting supports 96 and 98 are pivoted together to close the aperture. The collected wastes which are segregated from the patient in the storage container may be solidified to a gel-like mass by the gelling material 147 in the waste collecting bag 126. An optional automated mechanism may be utilized to dispense pellets of gelling material at periodic intervals such as upon activation of the bidet. Any odors which are not masked by the deodorant in the gelling material may be contained within the storage container by simply delivering an air stream through conduit 180 to opening 178. This creates a slight positive pressure which prevents odors from drifting up through drain opening 170.

Support structure 20 and waste collection apparatus 82 permit patient defecation and cleaning to be easily accomplished without requiring assistance from nursing personnel. The patient may operate the controls 187*a* to elevate the interfacing saddle 88 through aperture 38 without the physical exertion which would be required to position a bed pan beneath the patient. Each time the waste collection apparatus 82 is needed it is readily available. Cleanup and drying may also be easily accomplished with little effort by the patient. When the collection apparatus 82 is no longer required, it is simply lowered out of sight without requiring repositioning of the patient.

Another important feature of the waste collection apparatus 82 is the manner in which the excreted wastes are collected and stored to minimize exposure of nursing personnel to risk of cross-contamination. The apparatus 82 provides a closed system for collecting the wastes and conveying them to a storage container remote from the individual for subsequent disposal. Nursing personnel are not needed during utilization of the apparatus by the patient and the waste collecting bag 126 is preferably sized for holding an accumulation of wastes so that disposal of apparatus 82 need take place only at periodic intervals.

When disposal of the storage container 84 with the waste accumulated therein is required, the saddle 88, conduit 86, and apron 184 are also disposed of. Tubing 152 and conduit 180 are disengaged from the saddle and the saddle, conduit 86 and apron 184 are then inserted into the disposal well 130 in container 84 and the sealing lid 123 is applied to seal the internal components of container 84. The container may then be transported to a suitable disposal site without risk of spillage of the contents. A new waste collection apparatus may then be positioned on platform 90 within the internal compartment 92 provided in support structure 20. The apparatus may be quickly assembled by simply positioning apron 184 and connecting conduit 86 to interface connector 146 and to saddle 88. The necessary connections are also made for the tubing 152 and conduit 180.

Figure 7:
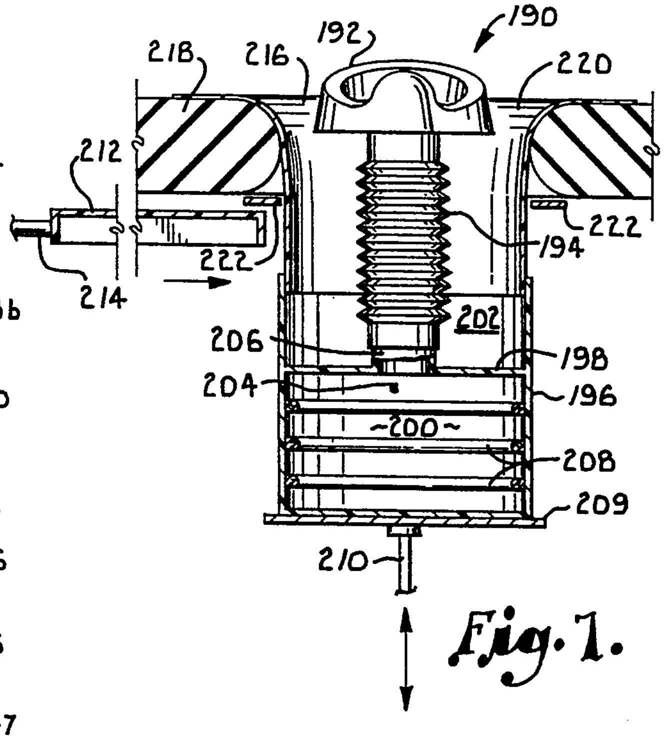
FIG. 7 is a vertical cross-sectional view of an alternate embodiment of the waste collection system.

Turning now to FIG. 7, an alternate embodiment of a waste collection apparatus 190 will now be described. Apparatus 190 comprises a patient interfacing saddle 192 connected by conduit 194 to a storage container 196. Saddle 192 is preferably constructed of materials and in a manner previously described in conjunction with saddle 88. Conduit 194 is preferably of rigid construction to support the saddle but is collapsible upon exertion of sufficient compression force. An inner surface of the conduit may also include a material having a low coefficient of friction.

Storage container 196 is of cylindrical or other construction and includes a divider 198 for separating the container into a lower waste storage compartment 200 and an upper compartment 202 for disposal of saddle 192 and conduit 194. A central opening 204 is provided in divider 198 and is surrounded by a fitting 206 which is coupled with a lower end of conduit 194. A plurality of rings 208 comprising a gelling material are vertically spaced on the inner surface of the container to solidify wastes which are accumulated within the container. Various types of gelling material such as hygroscopic substances may be utilized.

The storage container 196 is supported on a platform 209 which is connected to a vertically extensible linear actuator 210. A lid 212 for the container is coupled with a horizontally reciprocating shaft 214 which aligns the lid with container 196 when the container is sealed prior to disposal.

An aperture 216 is provided in a mattress 218 overlying the waste collection apparatus. A suitable opening mechanism such as mechanism 40 previously described may be included for opening and closing aperture 216. An apron 220 is provided to cover a portion of the top surface of mattress 218 and extends through aperture 216. Apron 220 is preferably of sufficient length to extend within the upper compartment 202 of container 196 when it is in an elevated position. A pair of closure platens 222 are positioned immediately below mattress 218 and are spaced apart so that they engage the top surface of lid 212 when it is reciprocated into vertical alignment with container 196.

In use, apparatus 190 may be operated in a manner similar to that previously described in conjunction with waste collection apparatus 82. Saddle 192 is elevated through aperture 216 to engage the patient's buttocks by vertical extension of platform 209. Wastes excreted into saddle 192 are then conveyed through conduit 194 into the lower compartment 200 of container 196.

The platform 209 is raised and lowered as needed to position the saddle. When the accumulated wastes are to be disposed of, the platform is lowered so that saddle 192 is positioned in a plane beneath that of container lid 212. Apron 220 is inserted into upper compartment 202 of container 196 and container lid 212 is then reciprocated into vertical alignment with the container. The container is then elevated to bring saddle 192 into contact with the lid. Upward movement of the lid is prevented by platens 222 and continued upward movement of the container causes compression of conduit 194 so that saddle 192 and conduit 194 are compressed into upper compartment 202. The lid 212 then seats on the container to seal the contents. Platform 209 may then be lowered and the container with its sealed contents disposed of in a suitable manner.

Figure 8:
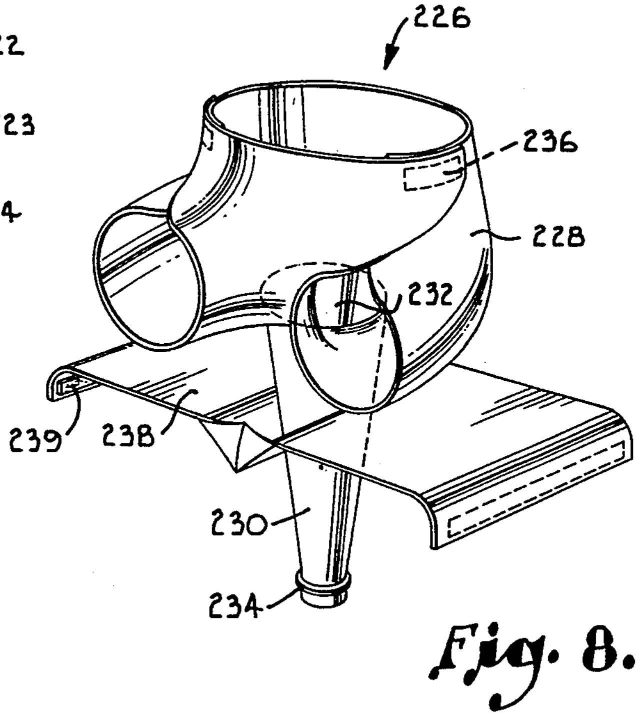
FIG. 8 is a front perspective view of a portion of another embodiment of the waste collection system.
Figure 14:
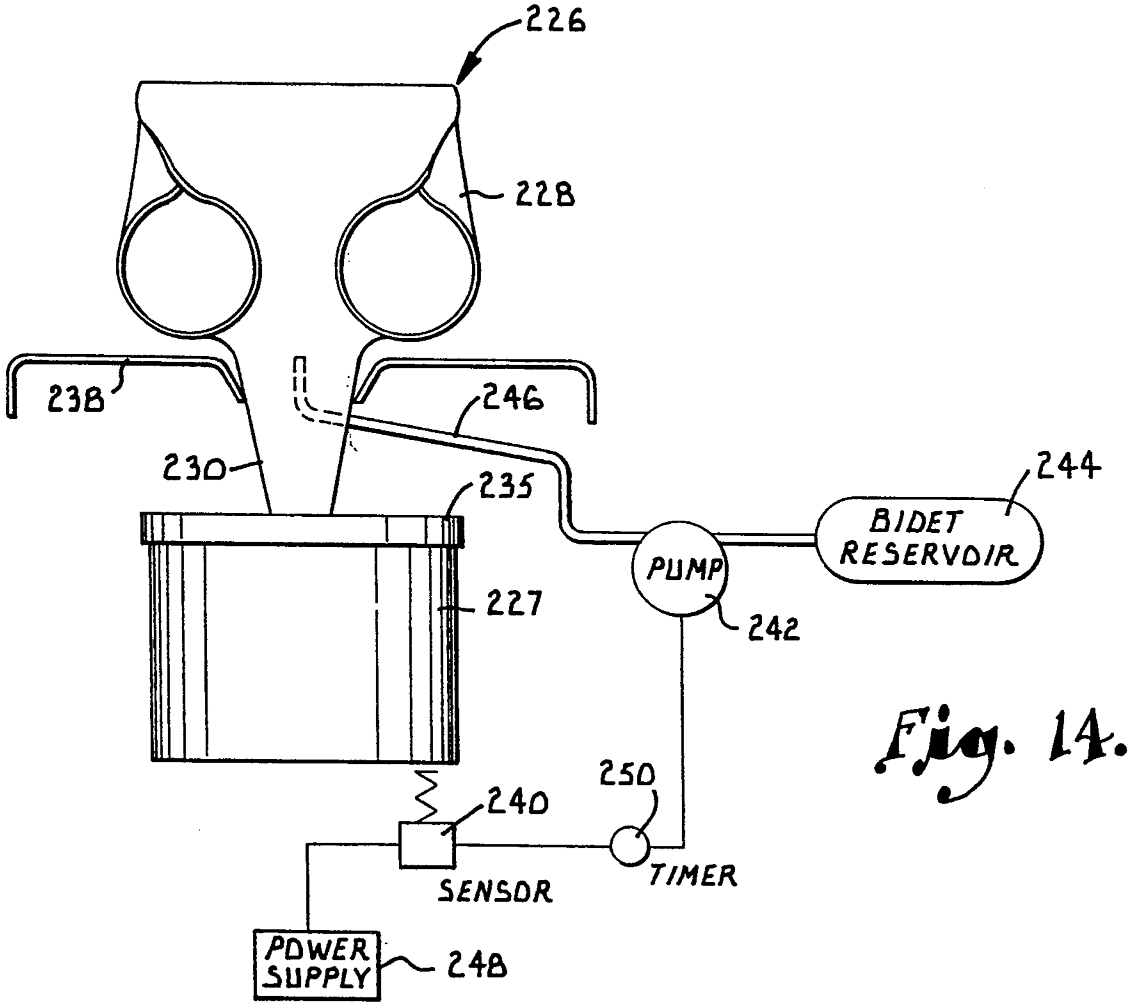
FIG. 14 is a front elevational view of a waste collection system, a portion of which is illustrated in FIG. 8.

Turning now to FIGS. 8 and 14, another embodiment of a patient interfacing device will now be described. A disposable device adapted for use by patients unable to control their bowel movements is represented broadly by the numeral 226. Device 226 is sued with a suitable storage container 227 and comprises a garment 228 and an attached conduit 230 of flexible construction. When in a flat, unfolded position, garment 228 has a generally hourglass configuration and may be attached to the patient's lower torso in a manner much like a disposable diaper. Garmet 228 may be formed from a variety of materials suitable for contact with a patient's skin.

An opening 232 is formed in a bottom panel of the garment 228 and an upper edge of conduit 230 is attached to the material surrounding opening 232. A fitment ring 234 is provided at a lower end of conduit 230 for coupling with a suitable connector provided in the storage container 227. An aperture in a lid 235 of the container is provided for receiving the lower end of the conduit.

The device 226 is preferably used in combination with support structure 20 previously described in connection with FIGS. 1 and 2. Releasable fastening tabs 236 such as Velcro® fasteners are positioned on the front and rear panels of the garment and an apron 238 with connector strips 239 is provided to shield the mattress upper surface. When garment 228 is fastened to the patient, opening 232 is positioned immediately beneath the patient's anal region and provides a drainage conduit through mattress aperture 38 for conveyance of the excreted wastes to the storage container 227 positioned at a remote location.

As shown in FIG. 14, an automated system comprising a weight sensor 240 and a bidet pump 242 may be provided to flush waste matter throughout the conduit 230. The bidet pump is coupled with a reservoir 244 and a delivery tube 246 which extends within conduit 230. The weight sensor 240 is connected to a power supply 248 and is linked to the bidet pump through a timer 250.

In use, the garment is attached to the patient in the same manner that a diaper would be attached. The support structure 20 facilitates attachment of the garment to the patient as the foot portion 26 and head portion 22 may be moved to place the patient in the desired orientation. The apron 238 is positioned on the mattress and aperture 38 is then opened by opening mechanism 40 and the conduit 230 inserted down through the apron and open aperture and coupled with a suitable container such as either container 84 or 196 previously described. The aperture may be left in an open, partially closed or completely closed position. If the aperture is completely closed it must be opened each time that the patient has a bowel movement so it is preferably left in at least a partially open position to allow unobstructed passage of wastes through the conduit 230.

For those patients unable to activate the bidet pump 242, the weight sensor 240 provides a means for detecting when wastes enter the container 227 so that the bidet pump may be automatically activated. When the sensor 240 detects a weight increase in the container, the timer 250 is energized. If the patient does not activate the bidet pump controls within the predetermined period of time set in the timer, the bidet pump is then automatically activated upon expiration of the timer. If desired, an alarm such as an audible chime may be used to alert the patient that the bidet pump is about to be activated. This automatic cleansing feature not only prevents waste build-up within the conduit 230 but also reduces objectionable odors.

Unlike a conventional diaper, device 226 permits the conveyance of excreted wastes to a remotely positioned container for subsequent disposal at periodic intervals. The device does not require changing each time a patient has a bowel movement and may be left on the patient for a period of time until the storage container is in need of disposal. The garment 228 may then be removed by simply detaching fastening tabs 236 and stuffing the garment, apron 238 and conduit 230 through the open aperture and into the storage container for subsequent disposal. If it is desired to change garment 228 at more frequent intervals, the storage container may be sized to hold a plurality of garments, aprons and conduits.

Figure 2B:
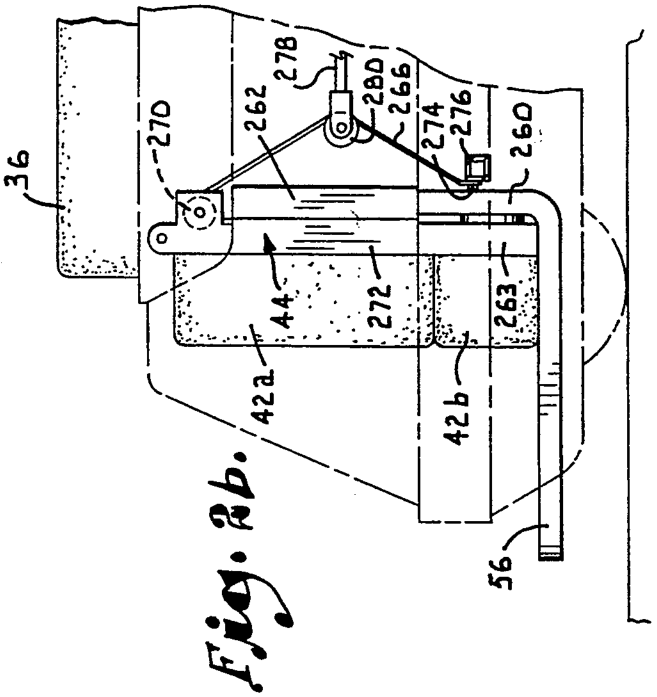
FIG. 2*b* is a side elevation view similar to FIG. 2*a* but showing the foot portion in a lowered position.
Figure 2C:
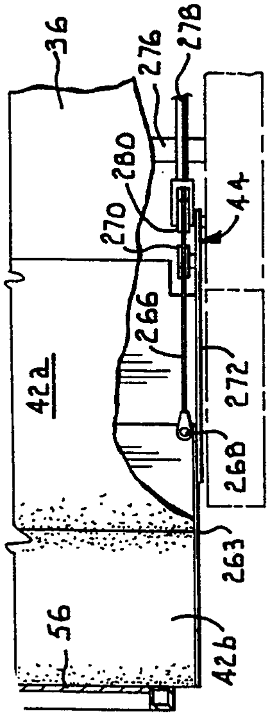
FIG. 2*c* is a fragmentary top plan view of the foot portion of the patient support structure taken along line 2*c*—2*c* in FIG. 2*a;*
Figure 2A:
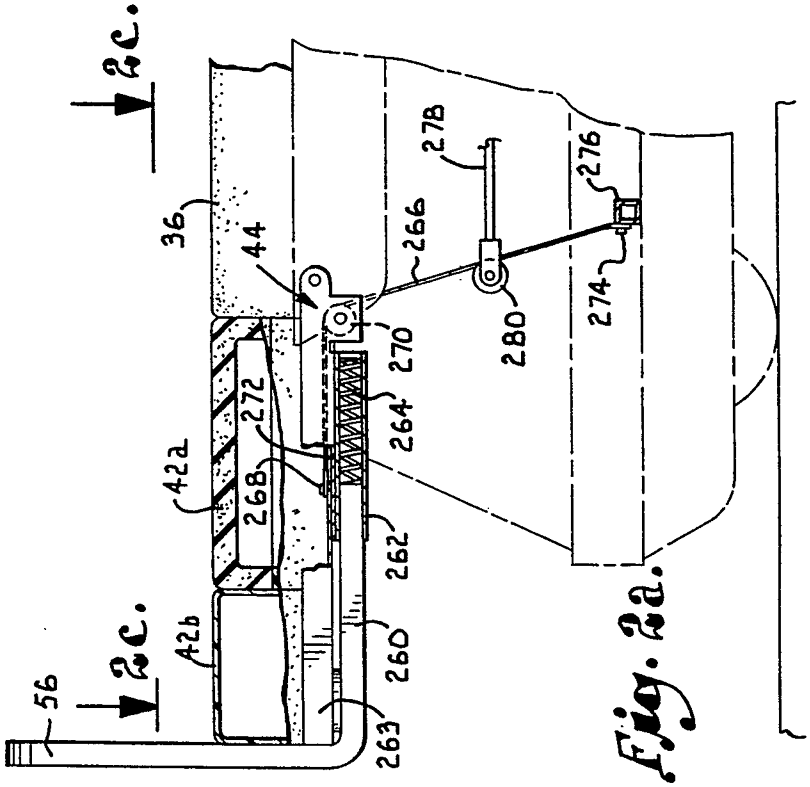
FIG. 2*a* is a side elevation view of the support structure showing a foot portion with positions broken away to illustrate details of construction.

Another important feature of the support structure 20 is illustrated in FIGS. 2*a–c*. The foot portion 26 telescopes outwardly when in the elevated position as shown in FIG. 2*a* to lengthen the surface for supporting a patient. When lowered to the position shown in FIG. 2*b* , the foot portion retracts. This retracting feature allows the support surface to be placed at the desired height above the floor surface to permit the patient to enter and exit the support surface while still providing a support surface of sufficient length to accommodate patients who require a long bed.

The telescoping function is provided by extension and retraction of foot rest arms 260 within sleeves 262 mounted to outer segment 272 of the hinged support frame 44. A spring 264 housed within each sleeve 262 provides a biasing force urging the foot rest and an attached outer frame segment 263 to an extended position. One end of a retraction cable 266 is attached to segment 263 of the frame by a pin 268. The cable is routed over a pulley 270 which is mounted on the inner segment 272 of frame 44 adjacent the pivoting axis of the foot portion 26. The other end of cable 266 is then attached by pin 274 to a transversely extending frame member 276. A retractable arm 278 which includes pulley 280 is coupled with cable 266 at a location intermediate pulley 270 and pin 274.

When foot portion 26 is elevated as shown in FIG. 2*a*, retractable arm 278 extends outwardly to slacken cable 266. The biasing force of springs 264 then urges foot rest arms 260 and frame segment 263 to an outwardly extended position. When the foot portion 26 is lowered to the position shown in FIG. 2*b*, the cable 266 is tensioned as a result of the pivoting movement of the foot portion as well as the retraction of arm 278. This causes arms 260 to retract within sleeves 262. Outer frame segment 263 also slides over inner frame segment 272 and results in shortening of the foot portion 26. Absent this shortening of the foot portion, the foot rest 56 would encounter the floor surface.

As the foot portion 26 is lengthened and shortened, the mattress segment 42*b* must also adjust to provide an uninterrupted surface of support for the patient's lower extremities. As can be seen in FIG. 2*a*, mattress segment 42*b* is of a relatively thin-walled construction when compared with segment 42*a*. These segments are preferably of an inflatable construction to provide a support surface of adjustable resiliency as will be subsequently described in greater detail. As the foot portion 26 is extended, the inflation of mattress segment 42*b* is increased to prevent any gaps between the mattress segment and foot rest 56. When the foot portion is maneuvered to its lowered position, the inflation of mattress segment 42*b* is reduced to maintain the top surface of the mattress segment in the same plane as the top surface of mattress segment 42*a*.

Figure 10:
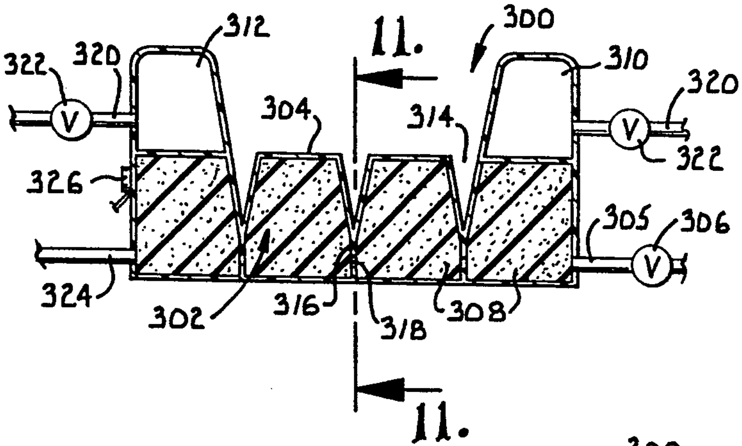
FIG. 10 is a vertical cross-sectional view of a mattress construction shown schematically.
Figure 11:
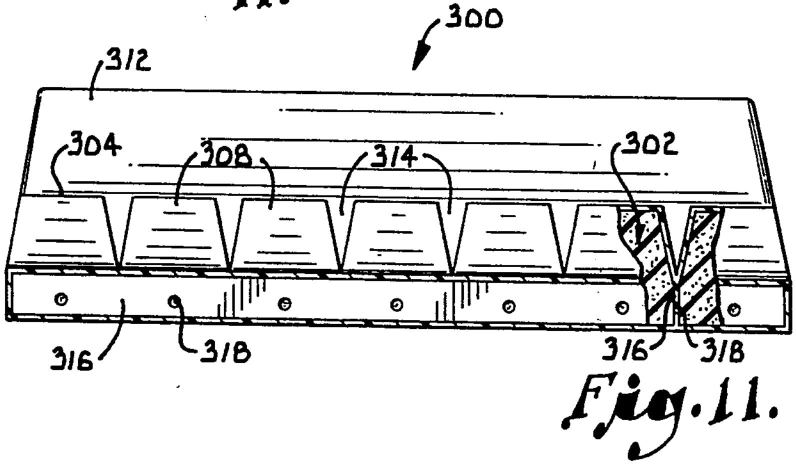
FIG. 11 is a vertical cross-sectional view of the mattress construction taken along line 11—11 of FIG. 10.

Turning now to FIGS. 10 and 11, a first embodiment of a mattress construction which may be used for one or more of the mattress sections of support structure 20 is represented broadly by the numeral 300. Mattress 300 includes an insert 302 which is in encased in an impermeable cover 304. The insert 302 is preferably formed from a light-weight, open-celled and permeable foam material but other materials having like properties may also be used. An air supply line 305 and pressure regulating valve 306 are provided to allow the resiliency of the foam insert 302 to be varied by selective inflation of the insert. A high volume air pump 307*a* and an air reservoir 307*b* (FIG. 13) are preferably used to inflate the mattress to the desired pressure with a minimum of pumping cycles.

Mattress 300 includes a plurality of individual support segments 308 and a pair of side retaining segments 310 and 312. Each support segment 308 is separated from an adjacent segment 308 by a V-shaped channel 314. The cover is securely attached to the exterior surfaces of each support segment 308 with vertical seams 316 extending between the support segments 308 to anchor the top portion of the cover to the bottom portion of the cover. Apertures 318 are provided to permit air flow through the seams 316.

The side retaining segments 310 and 312 extend above the support segments 308 located along the side edges of the mattress 300. Side retaining segments 310 and 312 comprise inflatable air chambers which are separated from the support segments 308 by the air impermeable cover 304. Both retaining segments 310 and 312 include an air supply line 320 and a pressure regulating valve 322.

An air return line 324 is coupled with mattress 300 to allow a continuous flow of temperature regulated air through the mattress support segments 308. A temperature sensor 326 is attached to tile cover 304 and is coupled with a heating and cooling mechanism which conditions the air delivered to the mattress 300.

In use, air is charged to the mattress through supply line 305 with air pressure within the mattress being regulated by valve 306. The permeable and open celled construction of the mattress insert 302 in combination with the enclosing cover 304 allows for passage of the air within the insert so that regulation of the air pressure regulates the resiliency of the insert. The mattress construction thus allows the resiliency of the insert 302 and mattress 300 to be selectively adjusted by varying the air pressure within the mattress. The resiliency of the mattress is preferably adjusted so that the patient is supported by the optimum pressure for reducing the incidence of pressure sores which commonly occur with bedfast individuals.

In the event that an accidental deflation of the mattress should occur, the foam insert 302 serves the important function of providing a resilient support surface for the patient. Without the foam insert, the patient would otherwise experience the discomfort of resting on the hard surface of the mattress support frame.

When side retaining segments 310 and 312 are inflated, they extend upwardly above the top surface of the support segments 308. When fully inflated it is preferred that the side retaining segments have a vertical dimension at least equal to that of the support segments 308 to significantly reduce the likelihood that the patient will inadvertantly roll of the mattress. Because of their resilient nature, the side retaining segments also reduce the likelihood of injury should the patient inadvertently bump into them.

Temperature regulation is another important feature of mattress 300. A continuous flow of temperature regulated air is provided to the mattress by circulating the air through supply and return lines 305 and 324. Temperature sensor 326 is provided to monitor air temperature within the mattress so that the body temperature of the patient may be regulated by increasing or decreasing the temperature of the circulating air. Temperature regulation not only increases the comfort of the patient but may also be of life saving importance in certain critical care situations.

Figure 12:
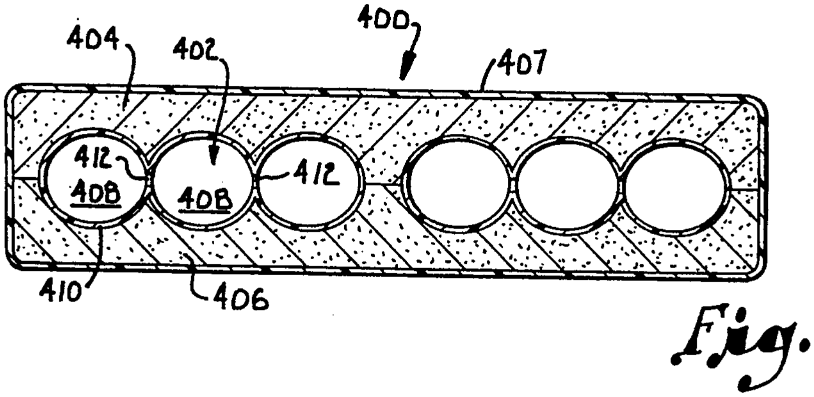
FIG. 12 is a vertical cross-sectional view of another embodiment of a mattress construction shown schematically.

Turning to FIG. 12, a modified embodiment of an air mattress is represented broadly by the numeral 400. Mattress 400 comprises an air inflatable region 402 sandwiched between foam inserts 404 and 406 encased in a cover 407. Air inflatable region 402 comprises a plurality of elongated air chambers 408 which have an oval cross-section when inflated. The air chambers 408 are formed by a air impermeable bladder 410 and may be interconnected by apertures 412 formed in the bladder. It may be desired to interconnect the air chambers in a manner to form two or more isolated air regions which may be independently inflated.

Inflation of mattress 400 to provide a resilient and temperature controlled support surface may be accomplished in the manner previously described in conjunction with mattress 300. Inflation of the mattress decreases the resiliency of the foam inserts 404 and 406 by compressing them into a smaller volume. Inflation of mattress 300 on the other hand decreases the resiliency of the foam insert 302 by increasing the air pressure within the foam itself. Like insert 302, should accidental deflation of the mattress occur, the foam inserts 404 and 406 provide a resilient support surface to prevent patient discomfort.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A replacement waste collection unit, comprising:
   - an outer canister including a closed bottom wall and at least one closed side wall having an upper edge, and a removable top wall having an aperture and a sealing lid removably closing said aperture;
   - an upstanding supporting liner disposed within said canister, said liner defining a central well;
   - a reservoir bag within said canister and straddling said supporting liner;
   - a waste receptacle bag within said canister and straddling said supporting liner; and
   - a patient interface, adapted for external engagement with an area at least partially surrounding a human anal region and adapted to be operatively connected to said receptacle bag, within the canister.

* * * * *